United States Patent [19]

Fujiwara

[11] 4,429,970
[45] Feb. 7, 1984

[54] ILLUMINATING LIGHT AMOUNT CONTROLLABLE RETINAL CAMERA

[75] Inventor: Hiroshi Fujiwara, Kawasaki, Japan

[73] Assignee: Olympus Optical Co., Ltd., Tokyo, Japan

[21] Appl. No.: 372,375

[22] Filed: Apr. 27, 1982

[30] Foreign Application Priority Data

Apr. 28, 1981 [JP] Japan ................................ 56-65073

[51] Int. Cl.³ .................. A61B 3/14; G03B 7/16; G03B 29/00
[52] U.S. Cl. .................... 354/413; 354/62; 351/206
[58] Field of Search .................. 354/32, 33, 62

[56] References Cited

U.S. PATENT DOCUMENTS

| 3,914,032 | 10/1975 | Takano et al. | 354/62 |
| 4,176,920 | 12/1979 | Ito | 354/62 |
| 4,264,153 | 4/1981 | Ito | 354/62 |
| 4,325,618 | 4/1982 | Hosoda | 354/62 |
| 4,331,403 | 5/1982 | Ohno | 354/62 |

FOREIGN PATENT DOCUMENTS 54-158093 12/1979 Japan .

Primary Examiner—Russell E. Adams
Attorney, Agent, or Firm—Cushman, Darby & Cushman

[57] ABSTRACT

A retinal camera wherein the illuminating light amount to the retina is made controllable so as to be of a proper value to make it possible to always obtain a retinal photograph of a proper exposure.

5 Claims, 2 Drawing Figures

ILLUMINATING LIGHT AMOUNT CONTROLLABLE RETINAL CAMERA

BACKGROUND OF THE INVENTION (a) Field of the Invention

This invention relates to retinal cameras and more particularly to an illuminating device for retinal cameras wherein the illuminating light amount to the retina is made controllable so as to be of a proper value.

(b) Description of the Prior Art

In a conventional retinal camera, in the case of strobo-photographing, as the object to be photographed is limited to a retinal part of an eye, the strobo-tube has been manually made to emit light while neglecting the difference in the reflection factor of the retinal part. However, in fact, the reflection factor is different depending on the eye to be inspected and, in the case of photographing the periphery of the retina, as the light bundle will be cut by the size of the pupil, the obtained photograph will not be always of a proper exposure. Even if the emitted light amount is corrected by assuming the cut of the light bundle, the operation will be difficult. Particularly, in a mass-diagnosis, the accuracy and operatability of the photographing are important. With a non-mydriasis retinal camera used recently in the mass-diagnosis, once the retina is photographed, the pupil will become so small that a time will be taken before it can be photographed again. Further, in the case of a natural mydriasis, the opening degree of the pupil will be so personally different that a cut will occur in some case and the exposure will be often wrong.

For the above reasons, it is generally desired to incorporate an autostrobo mechanism in a retinal camera. However, as the retina very low in the reflection factor is to be photographed, the exposure will be greatly influenced by the dispers and reflected lights within the eye, the light reflected on the cornea surface and the like. Such detrimental lights often appear from the periphery of the image plane. Particularly the dispersed and reflected lights at a wide angle are difficult to remove. Such detrimental lights are likely to enter the periphery of the image plane. Therefore, the light measuring range in the autostrobo-photographing had better be limited to be in the center part of the image plane. However, the reflection factor of the retina is not uniform. Particularly, the reflection factor of the nipple part is much higher than in any other part. Depending on the light measuring range, the exposure will be influenced by the variation of the nipple position with respect to the image plane.

SUMMARY OF THE INVENTION

In view of the above mentioned circumstances, a primary object of the present invention is to provide a retinal camera wherein the illuminating light amount to the retina is made to be always of a proper value, that is, the light amount of the illuminating light source is made to be always of a proper value.

According to the present invention, this object is attained by making the light measuring range of the retina at least 2.5 times as large in the diameter as the nipple part in a retinal camera wherein a part of the light from the retina is detected with a light receiving element and the light amount of the illuminating light source is controlled on the basis of this detected light amount.

According to a preferred formation of the present invention, a light receiving lens and a stop are arranged in front of a light receiving element and the light measuring range is determined by the magnification of the light receiving lens and the diameter of the stop.

According to the present invention, the light can be measured without being influenced by the detrimental lights and nipple and a photograph of a proper exposure can be thereby always obtained.

According to another preferred formation of the present invention, the light receiving element is connected to a photographing light source through an integrating section, control section and light emission control section and the light amount of the photographing light source is controlled to be always of a proper value on the basis of the light amount detected by the light receiving element. If the light receiving element is connected to an observing light source through the integrating section, control section and light emission control section, the light amount of the observing light source will be able to be likewise controlled to be always of a proper value.

Thus, there is no need of manually adjusting the complicated exposure amount and a retinal camera very convenient for clinics can be provided.

This and other objects of the present invention will become more apparent during the course of the following detailed description and appended claims.

DESCRIPTION OF THE PREFERRED EMBODIMENT

Figure 1:
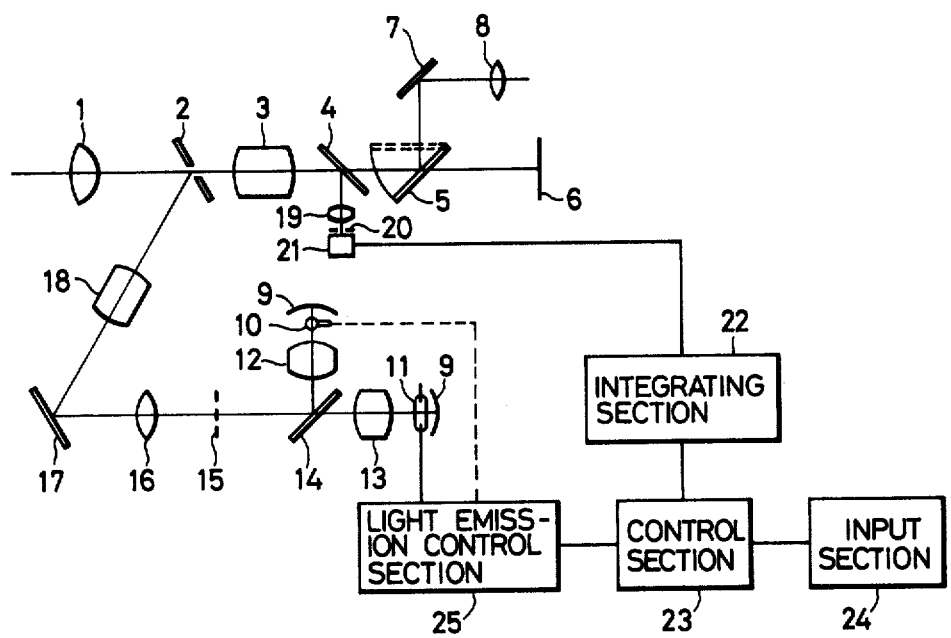
FIG. 1 is a view showing a formation of a retinal camera according to the present invention.

The detailed contents of the present invention shall be explained on the basis of the illustrated embodiment in the following. In FIG. 1, the reference numeral 1 denotes an objective, 2 denotes a reflecting mirror having a central opening, 3 denotes a photographing lens, 4 denotes a half mirror, 5 denotes a quick-return mirror, 6 denotes a film surface, 7 denotes a reflecting mirror and 8 denotes an eyepiece. These form a photographing and observing system. The reference numeral 9 denotes a reflecting mirror, 10 denotes an observing light source, 11 denotes a photographing light source, 12 and 13 denote light collecting lenses, 14 denotes a half mirror, 15 denotes a ring slit, 16 and 18 denote release lenses and 17 denotes a reflecting mirror. These form an illuminating system. In the optical system of such formation, as well known, the light from the observing light source forms a light source image on the ring slit 15 by the light collecting lens 12. Further, the light having passed through the ring slit 15 forms a ring slit image near the reflecting mirror 2 by the relay lenses 16 and 18, passes through the objective 1 and illuminates the eye to be inspected in the form of a ring. In the same manner, the light from the photographing light source also illuminates the retina. The light from the illuminated retina passes through the objective 1 and the central opening of the reflecting mirror 2 and forms an image on the film surface 6 (when the mirror 5 is in the position indicated by the dotted lines) by the photographing lens 3 or an observation is made with the eyepiece 8 (when the mirror 5 is in the position indicated by the solid lines). Here, a part of the light reflected by the half mirror 4 forms a retina image on the light receiving element 21 by the light receiving lens 19. A stop 20 is arranged in front of the light receiving element 21 to thereby determine the light measuring range of the retina. The photoelectric current from the light receiving element 21 passes through an integrating section 22, becomes a controlling signal by the film sensitivity information, exposure correcting information and manual switching information from an input section 24 in a control section 23 and controls the light emission of the strobo by a light emission control section 25.

In such formation as in the above, according to the present invention, a proper exposure can be obtained in any case by making the light measuring range in a specific range by making the magnification of the light receiving lens 19 and the diameter of the stop 20 of some values.

Figure 2:
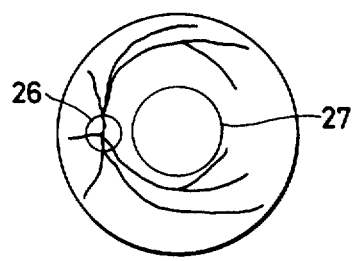
FIG. 2 is a view for explaining the relation between a light measuring range and a nipple.

FIG. 2 is a view showing a retina part. The reference numeral 26 denotes a nipple and 27 denotes a light measuring range. Now, if the average retina reflection factor is represented by R, the diameter of the nipple is represented by D, the magnification of the light measuring range to the nipple is represented by $\alpha$ and the magnification of the nipple reflection factor to the average retina reflection factor is represented by $\beta$, the reflected light amount IN of the nipple part and the reflected light amount IG within the light measuring range will be respectively $IN = (\pi/4)D^2\beta R$ and $IG = (\pi/4)\alpha^2 D^2 R$. Therefore, the variation K between the reflected light amount (exposed light amount) in case the nipple enters the light measuring range and the reflected light amount (exposed light amount) in case the nipple does not enter the light measuring range will be as shown by the following formula:

$$K = \frac{\left(IG - \frac{\pi}{4}D^2R + IN\right) - IG}{IG} = \frac{\beta - 1}{\alpha^2}$$

Generally, in a reversal film, as $\frac{1}{3}$ of the exposed light amount variation can be allowed, if $$K = \frac{\beta - 1}{\alpha^2} < \frac{1}{3},$$

even if the exposed light amount varies, the photographing will not be adversely influenced.

$\alpha > \sqrt{3(\beta - 1)}$ from $$\frac{\beta - 1}{\alpha^2} < \frac{1}{3}$$

of the above formula. Therefore, if $\beta$ is known, the light measuring range will be able to be determined. As a result of the measurement, it is found that the average reflection factor of the entire nipple part is about 3 times as large as the average retina reflection factor. Therefore, $\beta$ may be considered to be $\beta = 3$. If $\alpha > 2.5$ from $\alpha > \sqrt{3(\beta - 1)}$ and $\beta = 3$, there will be no influence of the nipple. Therefore, in the optical system shown in FIG. 1, if the light measuring range of the light receiving element 21 is made at least 2.5 times as large in the diameter as the nipple by the magnification of the light receiving lens 19 and the diameter of the stop 20, the light will be able to be measured without being influenced by the nipple. Therefore, according to the embodiment of the present invention, the light measuring range of the retina receiving the light with the light receiving element is selected to be 2.5 times as large in the diameter as the nipple (the diameter of the light measuring range is 2.5 times as large as the diameter of the nipple).

By the way, it is evident that the present invention is not limited to the light measuring method described in the embodiment but can be modified to measure the light, for example, on a film surface.

I claim:

1. A retinal camera comprising a light receiving element which can receive a part of the light from the retina and an illuminating light source which is arranged to illuminate said retina and can have the emitted light amount controlled on the basis of the light amount detected by said light receiving element, the light measuring range of said retina being made at least 2.5 times as large in the diameter as the nipple of the retina.

2. A retinal camera according to claim 1 wherein said retinal camera further comprises a light receiving lens and stop arranged in front of said light receiving element and said light measuring range is determined by the magnification of said light receiving lens and the diameter of said stop.

3. A retinal camera according to claim 1 or 2 wherein said retinal camera further comprises an integrating section connected to said light receiving element, a control section connected to said integrating section and a light emission control section connected to said control section and said light emission control section is connected to said illuminating light source.

4. A retinal camera according to claim 3 wherein said illuminating light source is a photographing light source.

5. A retinal camera according to claim 3 wherein said illuminating light source is an observing light source.

* * * * *